US00PP34536P3

(12) United States Plant Patent
Olesen

(10) Patent No.: US PP34,536 P3
(45) Date of Patent: Sep. 6, 2022

(54) ROSE PLANT NAMED 'POULPAL090'

(50) Latin Name: *Rosa hybrida*
Varietal Denomination: Poulpal090

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,611

(22) Filed: Sep. 7, 2021

(65) Prior Publication Data

US 2022/0095509 P1 Mar. 24, 2022

(30) Foreign Application Priority Data

Sep. 21, 2020 (QZ) ..... PBR 2020/2258

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148, 101, 141
See application file for complete search history.

(56) References Cited

PUBLICATIONS

Poulsen Roser A/S website for 'Bogor'. 2021. https://www.poulsenroser.dk/en/roses/ShowProduct/60320. 2 pgs. (Year: 2021).*

* cited by examiner

*Primary Examiner* — Susan McCormick Ewoldt
*Assistant Examiner* — Karen M Redden

(57) ABSTRACT

A new garden rose plant of the Compact Floribunda class which has abundant, pink flowers, strong perfume, and attractive foliage. This new and distinct variety has shown to be uniform and stable in the resulting generations from asexual propagation.

2 Drawing Sheets

Botanical designation: *Rosa hybrida.*
Variety denomination: 'Poulpal090'.

This application claims priority to Plant Breeder's Rights Application Number 2020/2258, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpal090', originated as a single seedling from the stated cross.

The new variety may be distinguished from its male pollen parent and female seed parent primarily by the following characteristics. The male pollen parent plant has flowers without perfume, while the new variety has strong flower perfume. The female seed parent plant has near white flowers while the new variety has pink flowers.

The objective of the hybridization of this rose variety was to create a new and distinct variety with unique qualities, such as:

1. Uniform and abundant pink flowers with strong perfume scent;
2. Vigorous, but compact growth when propagated on its own roots;
3. Exceptional disease resistance.

This combination of qualities is not present in previously available commercial cultivars of this type, known to the inventor, and distinguish 'Poulpal090' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpal090' was selected in the spring of 2012 by the inventor as a single plant from the progeny of the aforementioned hybridization.

Asexual reproduction of 'Poulpal090' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpal090' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal090'.

Specifically illustrated in FIG. 1 of the drawings are open flowers, petals detached revealing reproductive flower parts, sepals detached showing the receptacle shape.

Figure 1:
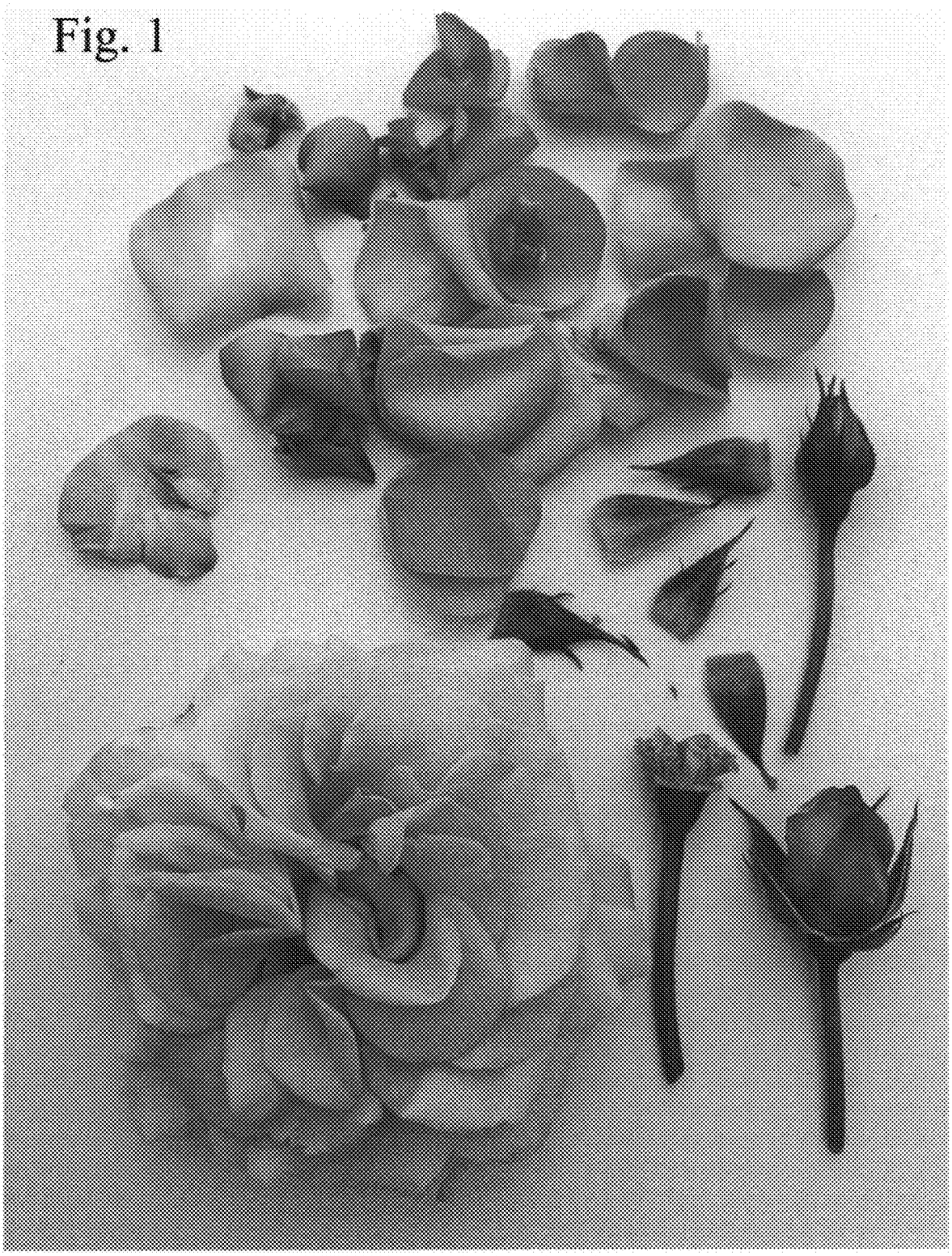
Figure 2:
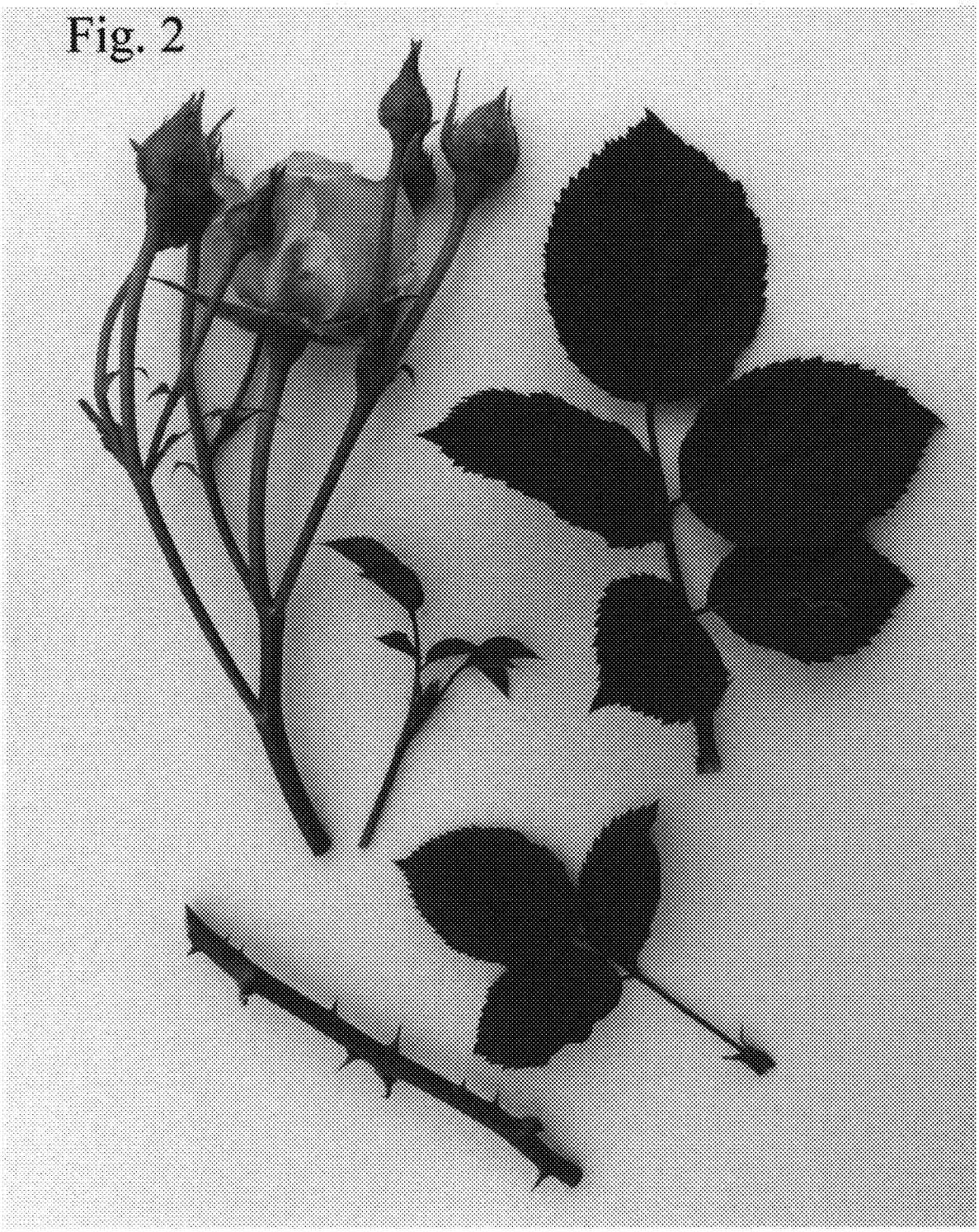

Specifically illustrated in FIG. 2 of the drawings are leaves, both juvenile and mature, bare stem showing prickles, and a cluster of flowers on the branch. Plants shown are 1 year old.

DETAILED DESCRIPTION OF THE VARIETY

The following is a description of 'Poulpal090', as observed in its growth in an open air container nursery in Odense Denmark. Observed plants are 1 year old and were grown on their own roots in 24 cm containers. Color references are made using The Royal Horticultural Society (London, England) Colour Chart, 2001, except where common terms of color are used.

For a comparison, several physical characteristics of the rose variety 'Poulpah086', U.S. Plant Pat. No. 29,701 are compared to 'Poulpal090' in Chart 1.

CHART 1

| | 'Poulpal090' | 'Poulpah086' |
|---|---|---|
| Petal Count | 70 | 40 |
| Flower Diameter | 85 mm | 55 mm |
| General Tonality of Flower Color | Red-Purple Group 65C and Red-Purple Group 62A | Red-Purple Group 62A |

Flower and flower bud:

*Blooming habit.*—Continuous.

*Flower bud.*—Size: Upon opening, 26 mm in length from base of receptacle to end of bud. Bud diameter is 16 mm. Bud form: Ovoid. Bud color: As sepals divide petals are Red-Purple Group 58C and Red-Purple Group 58A. Sepal inner surface: Color: Yellow-Green Group 146D. Surface: Lightly pubescent. Sepal outer surface: Color: Yellow-Green Group 144A with intonations of Greyed-Purple Group 187C. Texture: Smooth. Sepal Shape: Apex: Cirrhose. Base: Flat at union with receptacle. Sepal Margin: Margins have moderate foliaceous appendages on three of the five sepals. Sepal size: 30 mm long, 13 mm wide. Receptacle: Texture: Smooth. Size: 8 mm in height, 10 mm wide. Color: Yellow-Green Group 144A. Shape: Campanulate and funnel. Pedicel: Surface: Many stipitate glands. Length: 40 to 50 mm. Diameter: 3.5 mm on average. Color: Yellow-Green Group 144B. Strength: Strong. Peduncle: Length: 2 to 6 cm. Diameter: About 3 mm. Color: Yellow-Green Group 145A. Texture: Smooth.

*Flower bud development.*—Flower buds are borne in clusters of 3 to 7 flower buds per stem. Development as a panicle.

*Flower bloom.*—Fragrance: Strong perfume. Duration: The blooms have a duration on the plant of approximately 14 days. Petals fall cleanly away from plant after flowers have fully matured. Size: Flower diameter is 85 mm when open. Flower depth is 45 mm. Flower shape: Deep and open cup. Shape of flower, side view: The upper portion is flat convex. The lower portion is flat.

*Petalage.*—Under normal conditions, flowers have about 70 petals.

*General tonality of flower.*—Open flowers are Red-Purple Group 65C and Red-Purple Group 62A.

*Petal color.*—Upon opening, outer petals Upper surface: Red-Purple Group 62C with other intonations of Red-Purple Group 73D. Petal spot Yellow Group 4D. Lower surface: Red-Purple Group 65D with shades of Red-Purple Group 62B. Basal petal spot Yellow Group 4D. Upon opening, inner petals: Upper surface: Red-Purple Group N57D with intonations of Red Group 37D at the middle zone. Basal petal spot Yellow Group 4B. Lower surface: Red-Purple Group 62A splashed with Red-Purple Group 62D. Basal petal spot Yellow Group 4C.

*Petals.*—Petal Reflex: Slightly reflexed. Margin: Entire and uniform. No undulations. Shape: Broad and elliptic. Apex shape: Rounded. Base shape: Acute. Size: 43 mm (l)×50 mm (w). Texture: Smooth. Thickness: Average.

*Petaloids.*—Size: 12 mm (l) by 11 mm (w). Quantity: About 10. Shape: Elliptical with an acute base and rounded apices. Color: Red-Purple Group N57D with intonations of Red Group 37D at the middle zone of the upper surface. At the lower surface Red-Purple Group 62A splashed with Red-Purple Group 62D. Basal petaloid spot of Yellow Group 4C on both sides.

*Reproductive flower parts.*—Pollen: None observed. Anthers: Size: 2 mm in length. Color: Greyed-Orange Group 163B. Quantity: 55 on average. Filaments: Color: Yellow Group 4C. Length: 6 mm. Pistils: Length: 5 mm. Quantity: 25 on average. Stigmas: Color: Greyed-Yellow Group 160D. Styles: Color: Yellow-Green Group 145D. Location of stigmas: Inferior in location relative to the length of the filaments and the height of the anthers. Hips: None Observed.

Plant:

*Plant growth.*—Upright, bushy, very compact. Plants are 32 cm in height, and 39 cm wide.

*Stems.*—Color of juvenile growth: Yellow-Green Group 144B. Color of mature growth: Yellow-Green Group 144A. Length: Canes are about 15 cm from the base of the plant to the flowering portion. Diameter: About 5 mm. Internodes: On mature canes about 25 to 30 mm between nodes. Surface Texture: Young wood: Smooth. Older wood: Smooth.

*Long prickles.*—Incidence: 9 prickles per 10 cm of stem. Size: Average length of prickles on mature stems is 6 mm. Shape: Upper portion is linear. Lower portion is concave. Color: Juvenile prickles: Greyed-Purple Group 184A. Mature prickles: Greyed-Purple Group 184A.

*Plant foliage.*—Compound leaf: 115 mm (l)×80 (w). Quantity: About 3 leaves per 10 cm of stem on average. Leaf bearing angle to the stem: 45 degrees. Color of juvenile foliage: Upper side: Yellow-Green Group 144A intensely shaded with anthocyanin Greyed-Purple Group 183A. Lower side: Yellow-Green Group 144A intensely shaded with anthocyanin Greyed-Purple Group 183A. Color of mature foliage: Upper side: Yellow-Green Group 147A. Lower side: Yellow-Green Group 146B.

*Plant leaves and leaflets.*—Stipules: Size: 13 mm long, 4 mm wide. Quantity: 2 per compound leaf. Shape: Linear, slightly broad based with outward extending apices. Margins: Serrated. Color: Yellow-Green Group 144A. Petiole: Length: 25 mm. Diameter: 2 mm. Upper surface color: Yellow-Green Group 144A. Lower surface color: Yellow-Green Group 144A. Rachis: Length: 33 mm Upper surface color: Yellow-Green Group 144A. Lower surface color: Yellow-Green Group 144A. Leaflet: Quantity: Normally 5 leaflets. Margins: Serrated. Size: Terminal leaflets are about 51 mm long, 39 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

*Disease resistance.*—Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

*Cold hardiness.*—The variety is tolerant to USDA Cold Hardiness Zone 6.

*Heat tolerance.*—The variety has been found to be suitable for climate conditions found in the American Horticulture Society heat zone 7.

I claim:

1. A new and distinct variety of rose plant of the Compact Floribunda rose class named 'Poulpal090', substantially as illustrated and described herein, due to its abundant pink flowers, strong perfume, disease resistance, and extended period of bloom.

* * * * *